United States Patent
Mesaik et al.

(10) Patent No.: US 9,701,690 B2
(45) Date of Patent: Jul. 11, 2017

(54) MYRTOCOMULOACETALONE 1 AS AN ANTI-INFLAMMATORY AGENT

(71) Applicants: Muhammed Ahmed Mesaik, Karachi (PK); Samreen Soomro, Karachi (PK); Farzana Shaheen, Karachi (PK); Noureen Khan, Karachi (PK); Zaheerul haq Qasmi, Karachi (PK); Sobia Ahsan Halim, Karachi (PK); M. Iqbal Choudhary, Karachi (PK)

(72) Inventors: Muhammed Ahmed Mesaik, Karachi (PK); Samreen Soomro, Karachi (PK); Farzana Shaheen, Karachi (PK); Noureen Khan, Karachi (PK); Zaheerul haq Qasmi, Karachi (PK); Sobia Ahsan Halim, Karachi (PK); M. Iqbal Choudhary, Karachi (PK)

( * ) Notice: Subject to any disclaimer, the term of this patent is extended or adjusted under 35 U.S.C. 154(b) by 0 days.

(21) Appl. No.: 14/219,875

(22) Filed: Mar. 19, 2014

(65) Prior Publication Data

US 2015/0266889 A1  Sep. 24, 2015

(51) Int. Cl.
C07D 493/14 (2006.01)
C07D 493/04 (2006.01)

(52) U.S. Cl.
CPC ................. C07D 493/04 (2013.01)

(58) Field of Classification Search
CPC .................................................... C07D 493/14
See application file for complete search history.

(56) References Cited

PUBLICATIONS

Myrtle, 2014, http://web.archive.org/web/20140215000850/http://www.anniesremedy.com/herb_detail39.php.*
Carta et al., 2008, caplus an 2008:161142.*
Werz et al., 2008, caplus an 2008:736454.*
Choudary et al., Organic Letters, 2013, 15, 1862-1865.*

* cited by examiner

*Primary Examiner* — Sun Jae Yoo
(74) *Attorney, Agent, or Firm* — Sarfaraz K. Niazi

(57) ABSTRACT

A novel compound Myrtocomuloacetalone 1 (MCA-1) exhibiting potent anti-inflammatory properties by inhibiting production of reactive oxygen species, including nitric oxide, superoxide, and hydrogen peroxide that effectively suppresses proliferation of T-cells and also reduces intracellular oxidative stress and inhibits NF kappa B activation.

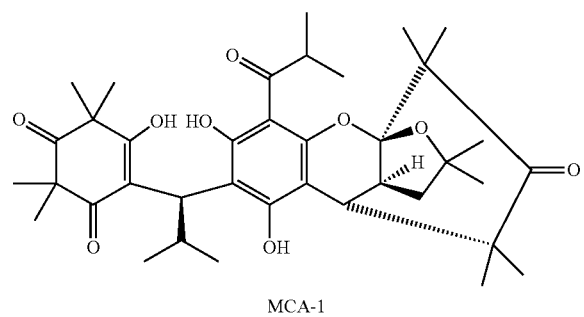

MCA-1

2 Claims, 9 Drawing Sheets

Merge

NF κ B

DAPI

Cells+ LPS     25 µg/mL     5 µg/mL     0.5 µg/mL

MYRTOCOMULOACETALONE 1 AS AN ANTI-INFLAMMATORY AGENT

BACKGROUND OF THE INVENTION

Reactive Oxygen Species (ROS) are diverse small signaling molecules which are highly reactive with unpaired valence electrons. ROS include superoxide ($O_2^-$), hydrogen peroxide ($H_2O_2$), hydroxyl radical (OH.), Nitric Oxide (NO) and peroxynitrite ($ONOO^-$). Although ROS have some physiological functions, excessive generation may lead to imbalanced homeostasis of the biological system. ROS are constantly generated through a variety of pathways, including both enzyme-catalyzed and nonenzyme reactions.

Whenever the balance between ROS generation and the natural antioxidant defense system is distributed, a series of events may occur, deregulating cellular functions, which may lead to various pathological conditions for almost all vital organs. Activated immune cells like macrophages neutrophils and microglia start overexpressing several enzymes, including iNOS, NADPH oxidase, COX-2, and myeloperoxidase responsible for inflammatory processes mediated by oxidative stress. These enzymes contribute to the pathogenesis of various diseases. ROS-Generating multimeric enzymes are indispensable for protecting the host against infections and injuries. However, inappropriate activation of these enzymes may be harmful in noninfectious autoimmune disorders. Thus the discovery of various novel agents that can inhibit the activation of these enzymes may be therapeutically significant in ameliorating various diseases, including rheumatoid arthritis, atherosclerosis and neurodegenerative diseases.

SUMMARY OF INVENTION

The invention features the immunomodulatory, particularly oxidative stress inhibiting composition, with no cytotoxic effects. Basic skeleton of this compound is pyroglucol with anti-inflammatory activity against innate and adaptive immune mediators. Current study deals with the effects of a compound on reactive oxygen and nitrogen species generated by macrophages. Effect on transcription factor NF kappaB was also analyzed. Furthermore, their effects on T-cell proliferation was investigated. Molecular dynamic studies for ligand and receptor binding for iNOS enzyme were also conducted.

Oxidative burst inhibitor is the compound that inhibits the free radicals generation during phagocytosis, while Nitric Oxide inhibitor means inhibitor of nitrosative stress. On the other hand, an inhibitor of adaptive immune system actually inhibits the proliferation of T-cells.

DETAIL DESCRIPTION OF THE INVENTION

Phytochemical investigation on *Myrtuscommunis* Linn. resulted in the isolation of a novel compound, named as myrtocomuloacetalone 1 (MCA-1). The novel compound MCA-1 exhibited potent anti-inflammatory properties via inhibiting production of reactive oxygen species, including nitric oxide, superoxide, and hydrogen peroxide. Additionally, it effectively suppressed proliferation of T-cells. Study revealed that it also reduced intracellular oxidative stress and inhibited NF kappa B activation.

Figure 1:
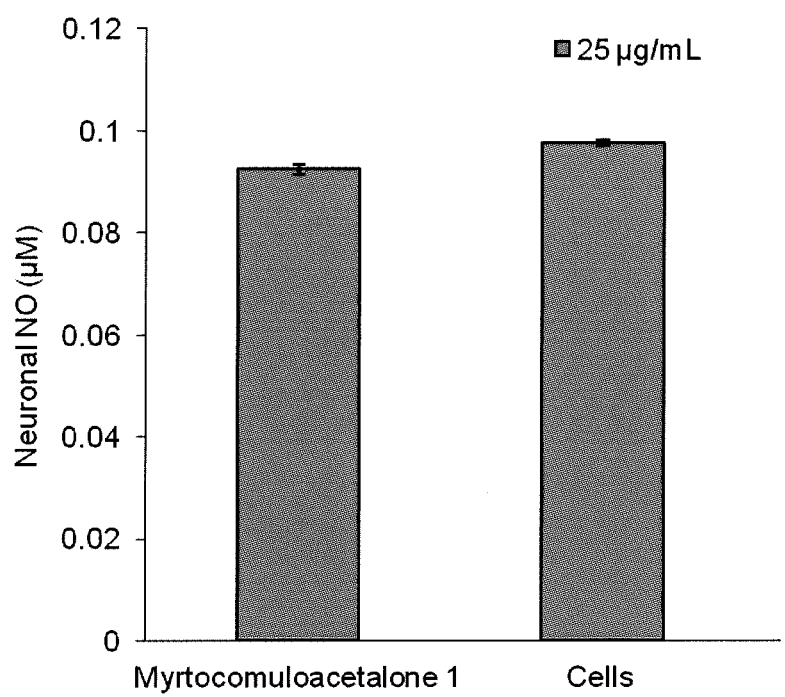
FIG. 1 depicts the effect of myrtocomuloacetalone 1 on basal level of Nitric Oxide neuronal cells. U138MG cells were incubated in presence and absence of compound for 48 hours and supernatant was analyzed for the level of the presence of nitrite by griess reagent.

Under normal physiological conditions, Nitric Oxide is necessary for normal vascular function because of its effect as a neurotransmitter. This kind of Nitric Oxide is called a basal level of Nitric Oxide, which is released by neuronal and endothelial synthases (Hattori, Kasai, and Gross 2004). The test compound does change in the basal level of Nitric Oxide released by the neuronal cell (FIG. 1).

Figure 2:
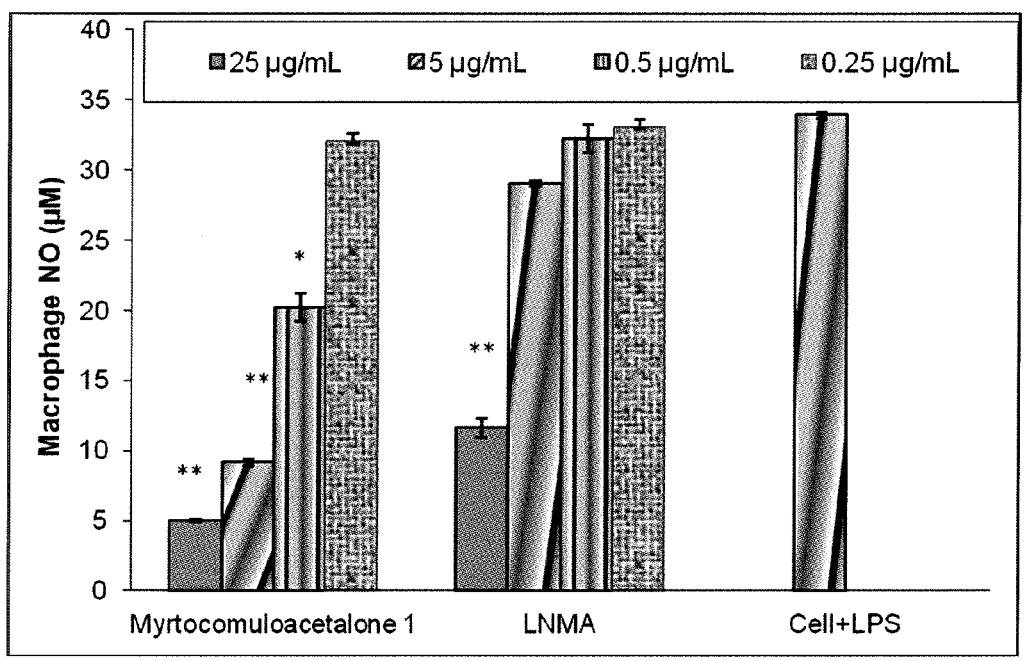
FIG. 2 depicts the effect of myrtocomuloacetalone 1 on inflammatory Nitric Oxide release by macrophages in response to LPS, macrophages. J774.2 cells were incubated in the presence or absence of compound for 48 hours and supernatant was detected for the presence of nitrite by griess reagent. The result was compared with known inhibitor of Nitric Oxide; LNMA (NG Monomethyl L arginine).

During inflammation, the inducible form of nitric oxide synthase gets activated and causes the robust generation of Nitric Oxide that causes excessive vasodilation which results in hypotension and septic shock. In contrast, Nitric Oxide combined with superoxide (ROS generated during phagocytosis) leads to ONOO generation and eventually reduces the bioavailability of basal Nitric Oxide and therefore normal function of neurotransition will be halted. This effect mainly leads to vasoconstriction, hypertension and atherosclerosis. Current studies reveal that the compound is an inhibitor to the inflammatory Nitric Oxide released by the activated macrophages in cell culture supernatant. It is found to be a highly significant inhibitor Nitric Oxide with an $IC_{50}$ value of <1 µg/mL (see FIG. 2).

Figure 3:
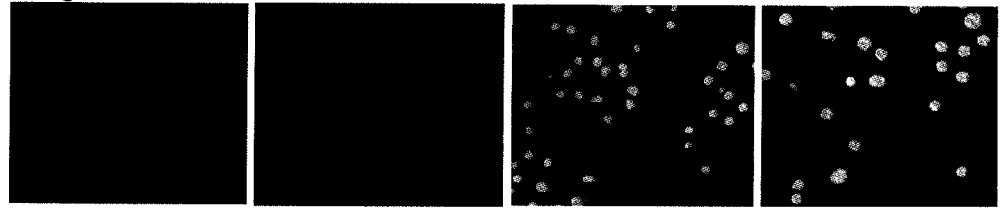
FIG. 3 depicts the LPS induced nuclear translocation of p65 subunit of NF kappa B in J774 cells. Effect of myrtocomuloacetalone 1 at concentration 25 µg/mL. Arrows show no transcription factor inside nucleus at 25 µg/mL, whereas 5, 0.5 µg/mL has no effect on nuclear factor translocation as compared to positive control. The cells were examined at 20× magnification under TRITC and DAPI channel using a Nikon TE-2000 epifluorescence microscope. Merging was done using Adobe Photoshop.
Figure 3:
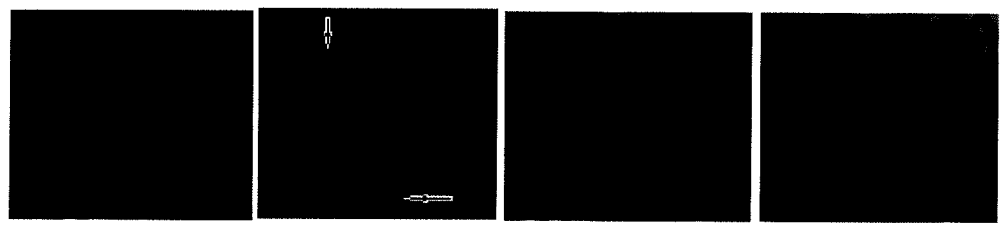
Figure 3:
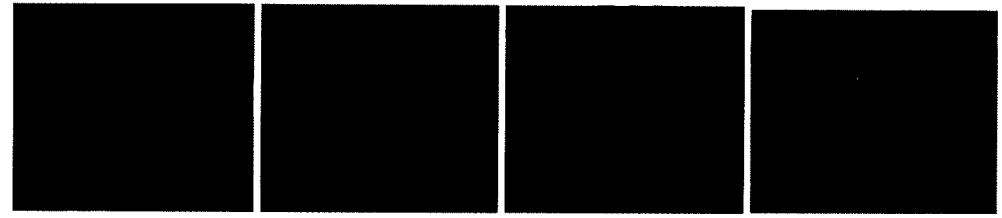

Myrtocomuloacetalone 1 completely inhibits the nuclear translocation of NF κB, which is a main transcription factor involved in Nitric Oxide production at 25 µg/mL. In contrast, the other transcription factor, p38, which is also activated by LPS, was found to remain unaffected. This result clearly indicates that the test compound is not having any affect at receptor level rather it is inhibiting the downstream signaling molecules involved in the process of Nitric Oxide production (FIG. 3).

The effect of compound (MCA-1) was checked for free radicals generated during oxidative burst analysis and it was found that the test compound has no effect on HOCl production, whereas it has profound effect on superoxide and hydrogen peroxide production (Table 1).

TABLE 1

Effect of myrtocomuloacetalone 1 on ROS and T-cell proliferation

| Compounds | ROS (HOCl) ($IC_{50}$) µg/mL | Oxidative burst % Inhibition 25 µg/Ml $O^{-2}$ | $H_2O_2$ | T-Cell proliferation ($IC_{50}$) µg/mL |
|---|---|---|---|---|
| Myrtocomuloacetalone (1) | >100 | 42.5 | 53 | <0.5 |
| Ibuprofen | 11.7 ± 1.8 | — | — | — |
| Prednisolone | — | — | — | <0.625 |
| Diphenyliodonium | — | 95 | — | — |

Figure 4:
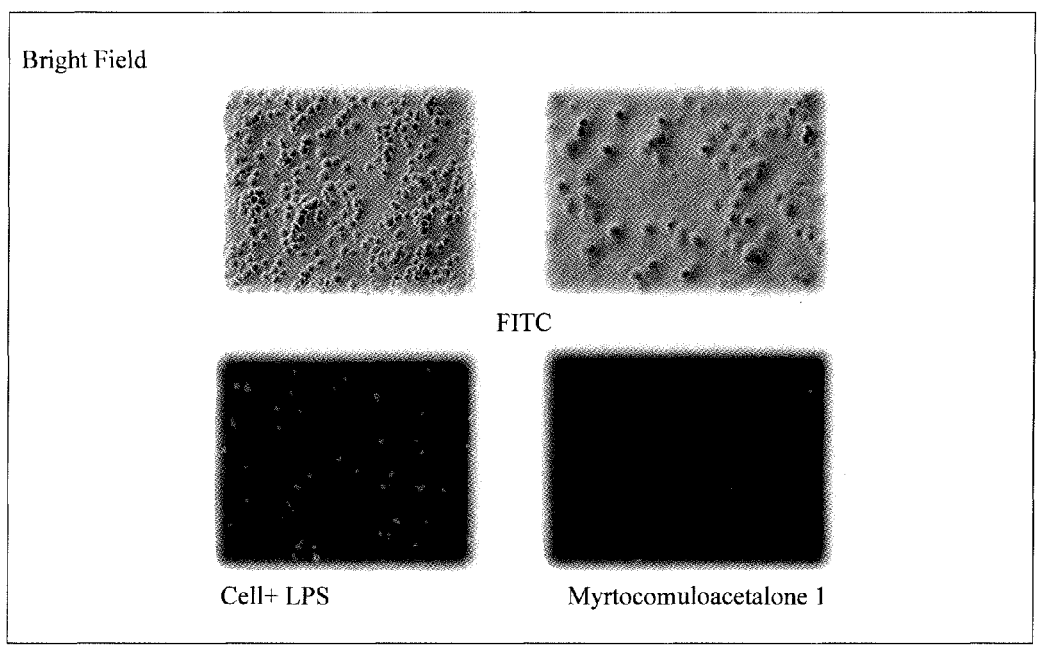
FIG. 4 depicts the intracellular oxidative stress examined by fluorescent microscopy. Mouse macrophage J774.2 cells, treated with phorbol myristate acetate (PMA) alone: positive control or in combination with compound. The cells were examined at 20× magnification under a green channel. Bright field images showing the total number of cells present in the same field were obtained under phase contrast at 20× magnification. Each image is representative of 3 individual experiments.
Figure 5:
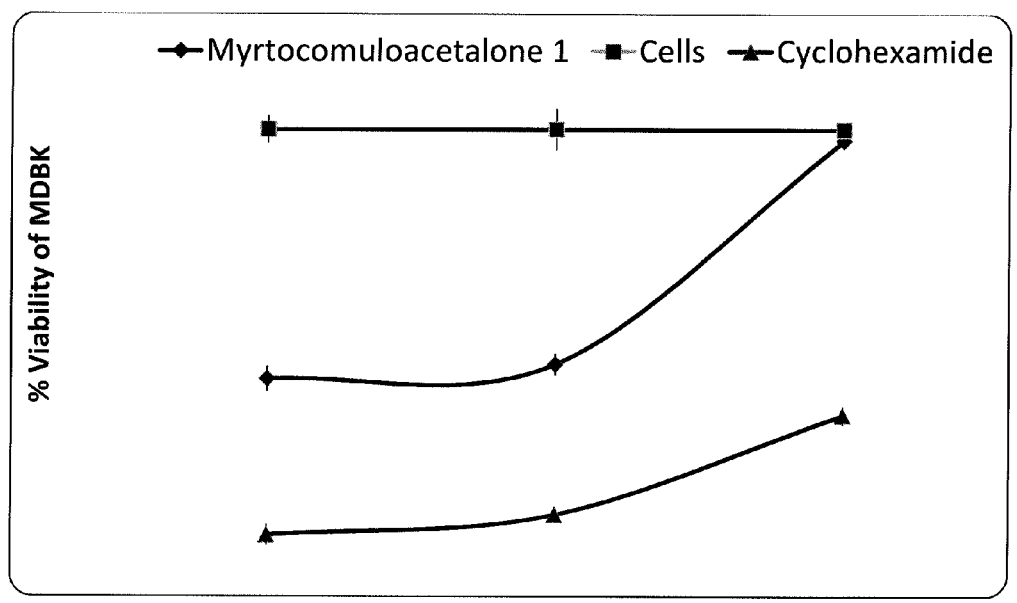
FIG. 5 depicts the effect of myrtocomuloacetalone 1 on MDBK kidney cell proliferation by MTT assay. MDBK Kidney cell line was incubated in the presence of three concentrations 25, 5 and 0.5 µg/mL of test compounds or without addition of compounds (– test control) and in presence of cytotoxic drug cyclohexamide (+ control).
Figure 6:
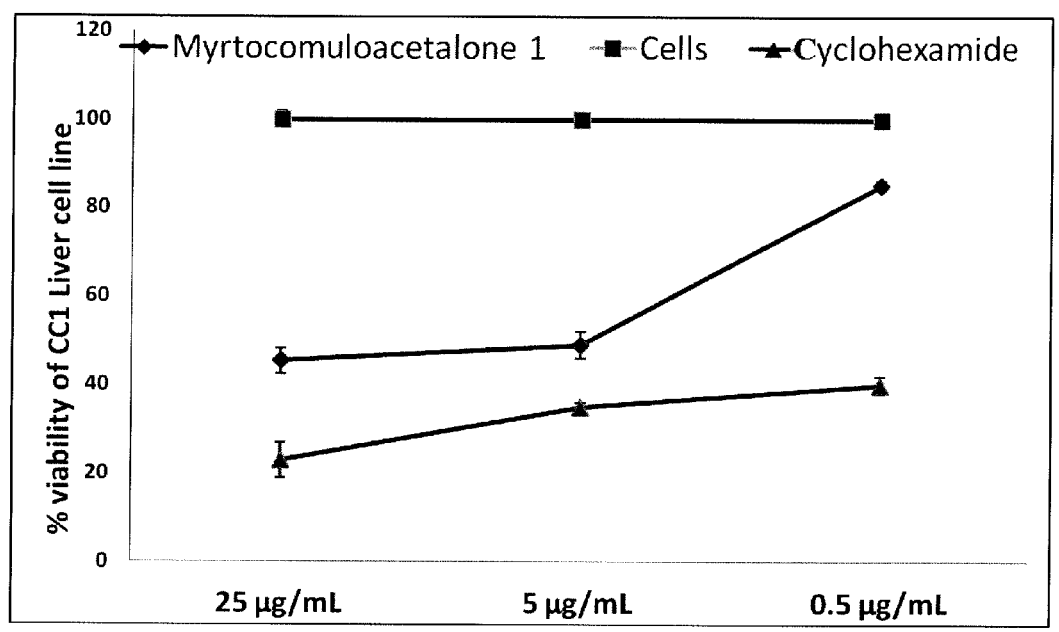
FIG. 6 depicts the effect of myrtocomuloacetalone 1 on Wistar rat CC1 liver cell proliferation by MTT assay. CC1 liver cellline was incubated in the presence of three concentrations 25, 5 and 0.5 µg/mL of test compounds or without addition of compounds (–ve control) and in the presence of cytotoxic drug cyclohexamide (+ control).
Figure 7:
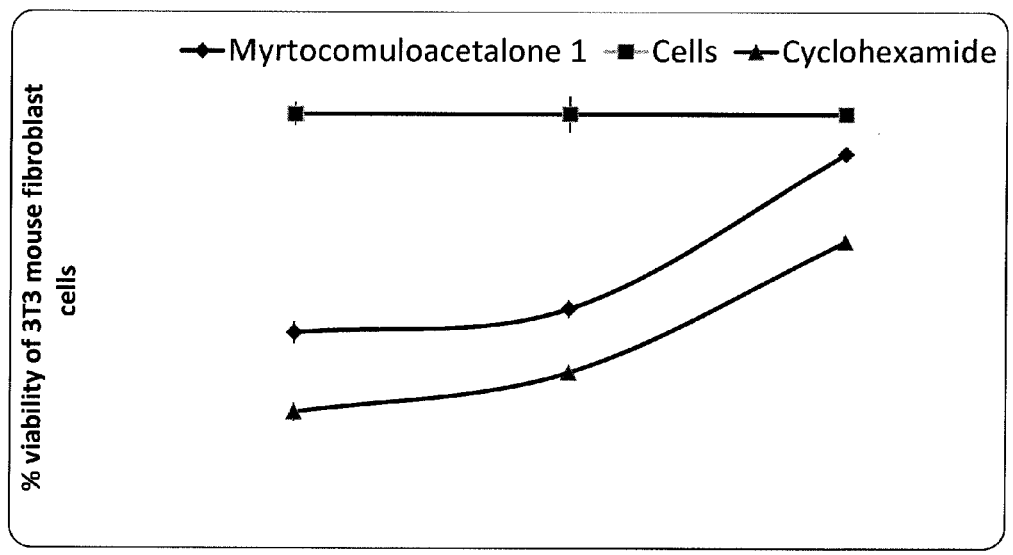
FIG. 7 depicts the effect of myrtocomuloacetalone 1 on 3T3 mouse fibrobast cell proliferation by MTT assay. Fibrobast cell line was incubated in the presence of three concentrations (25, 5 and 0.5 µg/mL) of test compounds or without addition of compounds (–ye control) and in presence of cytotoxic drug cyclohexamide (+ control).
Figure 8:
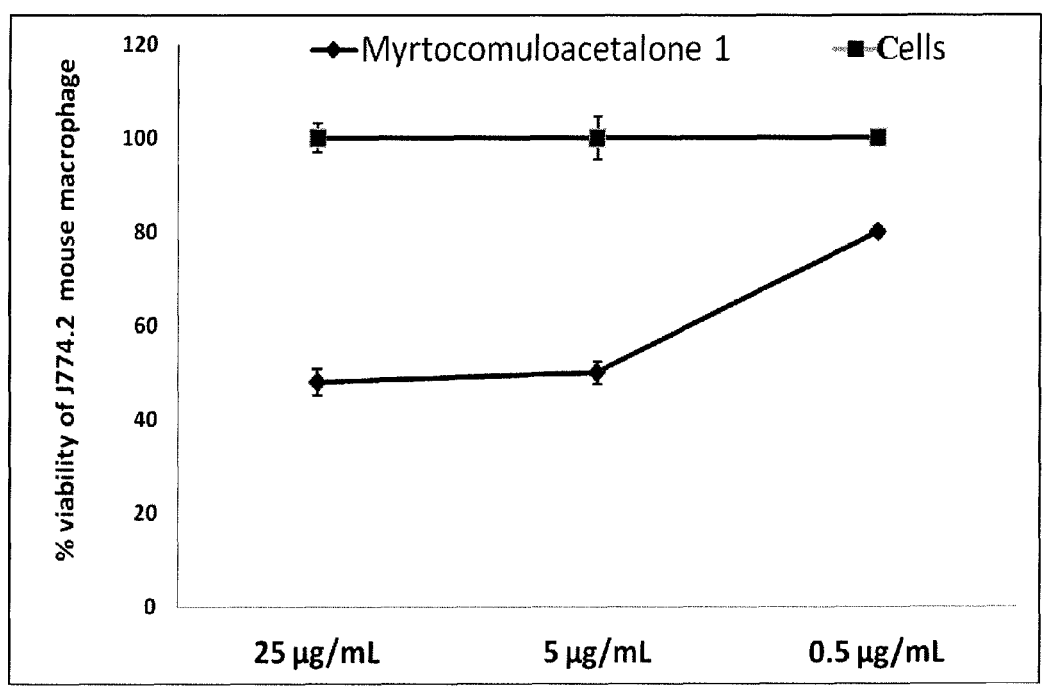
FIG. 8 depicts the effect of myrtocomuloacetalone 1 on J774.2 mouse macrophage cell proliferation by MIT assay. Macrophage cell line was incubated in the presence of three concentrations (25, 5 and 0.5 µg/mL) of test compounds or without addition of compounds (–ve control).

In order to validate the above mentioned results, we also investigated the effect of compound on intracellular ROS levels by using 2',7'-dichlorfluorescein (DCFH) dye, which mainly measures the $H_2O_2$ released into the intracellular environment. We employed PMA as a stimulant since PMA is known to activate the NADPH oxidase via protein kinase C pathway. Compound MCA-1 showed inhibitory effects only in the PMA induced ROS generation, but not zymosan induced ROS production of mainly HOCl (FIG. 4).

T Lymphocytes, the major key detector cells of the adaptive immune responses, differ entirely from those of innate immunity that includes free a radical generation system. However, the effector pathways overlap to a great extent. Therefore, they can play a leading role in the development of autoimmune disease related to oxidative stress. Our results indicate that myrtocomuloacetalone 1 is a significantly inhibiting proliferation of T cells with an $IC_{50}$<0.5 µg/mL (Table 1).

The effect of myrtocomuloacetalone 1 on cell viability was determined in MDBK, CC1, J774 and 3T3 Fibrobast cells and the $IC_{50}$ for each line was calculated. The data is presented in FIGS. 5-8. The $IC_{50}$ of Myrtocomuloacetalone 1 on these cell when incubated for 48 hours appear to be within 4-6 µg/mL range (MDBK kidney cells, 4.5±1.1 µg/mL; CC1 liver cells, 4.6±0.7 µg/mL; 3T3NIH mouse fibroblasts, 6.53±1.2 µg/mL; J774.2 macrophages 5±0.8 µg/mL). These compounds appear to be far less toxic compared to the cycoxehamide, which showed a IC50 of MDBK kidney cells, 1.2±0.4 µg/mL; CC1 liver cells, 0.02±0.001 µg/mL and 3T3 mouse fibroblast cells 0.13 µg/mL.

Docking simulations were performed to predict the binding mode of all the iNOS ligands in the murine iNOS active sites and to evaluate their binding affinities.

The most active iNOS inhibitor myrtocomuloacetalone 1 mediates several hydrogen bonding interactions with the surrounding residues at the active site including Gly369, Gln257, the side chain oxygen of heme, a three water molecules WAT 1312, 1321 and 1602.

Figure 9:
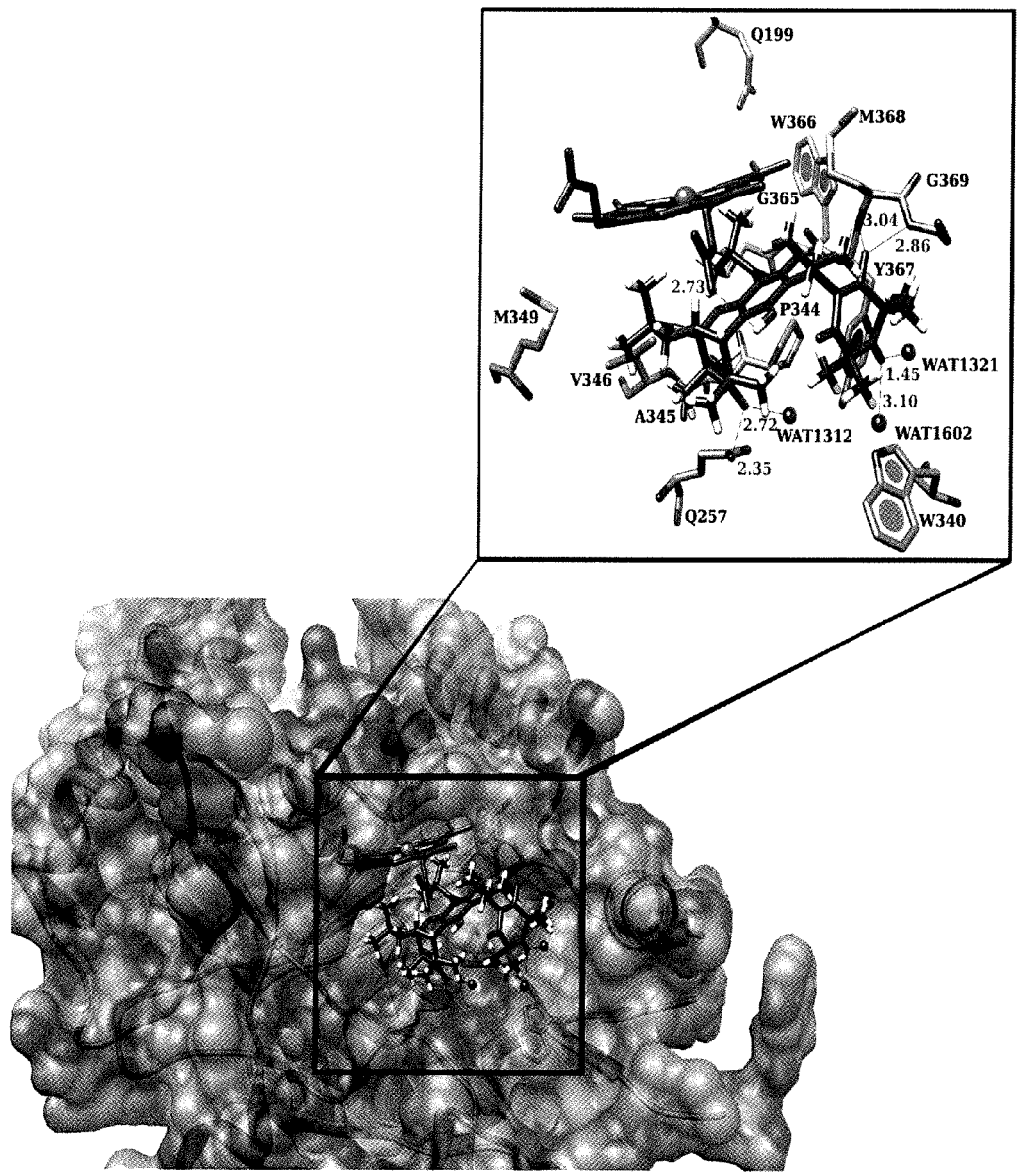
FIG. 9 depicts the 3D structure of murine iNOS and binding mode of myrtocomuloacetalone 1. The binding mode of most active compounds is shown in the box. The active site residues are depicted in coral sticks. The active site heme is shown in purple sticks while the myrtocomuloacetalone 1 is shown in green sticks.

A bi-dentate interaction was observed between the carbonyl oxygen at C-15 of myrtocomuloacetalone (1) and the side chain oxygen of Gln257 and WAT1312 at a distance of 2.35 Å and 2.72 Å, respectively. While the carbonyl oxygen at C-3' interacts with WAT 1321 and 1602 at a distance of 1.45 Å and 3.10 Å, respectively, the side chain oxygen of heme contributes in stabilizing the compounds by mediating hydrogen bonding with the hydroxyl group at C-7 position of myrtocomuloacetalonel (2.73 Å). Moreover, the compound is further stabilized by forming bidentate interactions with the amide nitrogen of Gly369 and Met368 at a distance of 2.86 and 3.04 Å, respectively. Molecular interactions of myrtocomuloacetalone 1 with the active site residues of iNOS are presented in FIG. 9.

This compound could play a role inthe treatment of autoimmune diseases, where T-cells are key players in initiating the organ rejection and on set of certain diseases. Additionally, it also could be an anti-inflammatory compound, particularly a molecule of choice where Nitric Oxide toxicity related disorders are suspected.

The invention claimed is:

1. A method of treating autoimmune disease of organ rejection comprising administering to patients in need of treatment a suitable quantity of myrtocomuloacetalone 1 comprising the structure:

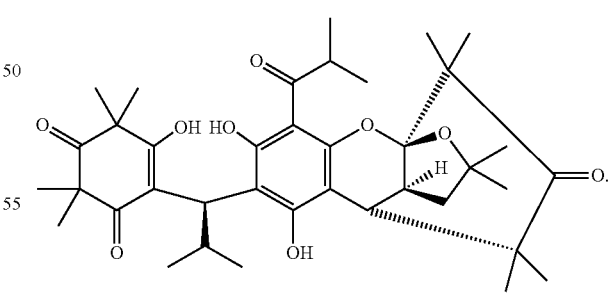

1

2. The method of claim 1, wherein pharmaceutical ingredients are added to myrtocomuloacetalone 1.

* * * * *